US009005894B2

(12) United States Patent
Ladner et al.

(10) Patent No.: US 9,005,894 B2
(45) Date of Patent: Apr. 14, 2015

(54) DETERMINATION OF KIR HAPLOTYPES ASSOCIATED WITH DISEASE

(75) Inventors: Martha Ladner, Oakland, CA (US); Elizabeth Trachtenberg, Berkeley, CA (US); Lloyd Gordon Bentley, Alameda, CA (US); Damian Goodridge, Darlington (AU); Henry A. Erlich, Oakland, CA (US)

(73) Assignees: Roche Molecular Systems, Inc., Pleasanton, CA (US); Childrens Hospital & Research Center at Oakland, Oakland, CA (US); Conexio Genomics Pty Ltd, Fremantle (AU)

( * ) Notice: Subject to any disclaimer, the term of this patent is extended or adjusted under 35 U.S.C. 154(b) by 0 days.

(21) Appl. No.: 12/884,602

(22) Filed: Sep. 17, 2010

(65) Prior Publication Data
US 2011/0129830 A1    Jun. 2, 2011

Related U.S. Application Data

(60) Provisional application No. 61/244,821, filed on Sep. 22, 2009.

(51) Int. Cl.
C12Q 1/68 (2006.01)
C12P 19/34 (2006.01)

(52) U.S. Cl.
CPC ............ *C12Q 1/6881* (2013.01); *C12Q 1/6883* (2013.01); *C12Q 2600/156* (2013.01); *C12Q 2600/16* (2013.01); *C12Q 2600/172* (2013.01)

(58) Field of Classification Search
USPC ............................................... 435/6.12, 91.2
See application file for complete search history.

(56) References Cited

U.S. PATENT DOCUMENTS

| 6,210,891 | B1 | 4/2001 | Nyren et al. | |
|---|---|---|---|---|
| 6,258,568 | B1 | 7/2001 | Nyren | |
| 6,274,320 | B1 | 8/2001 | Rothberg et al. | |
| 2008/0280289 | A1* | 11/2008 | Dinauer et al. | 435/6 |
| 2010/0086914 | A1* | 4/2010 | Bentley et al. | 435/6 |

FOREIGN PATENT DOCUMENTS

| WO | 2007041067 | A2 | 12/2007 |
|---|---|---|---|
| WO | 2009049889 | A1 | 4/2009 |
| WO | 2009051672 | A2 | 4/2009 |
| WO | 2009074326 | A2 | 6/2009 |
| WO | 2009074326 | A3 | 6/2009 |
| WO | PCTEP2010005721 | | 1/2011 |

OTHER PUBLICATIONS

Murdoch et al. Tissue Antigen, 2006, Journal complication, 2006, vol. 68,m p. 72-77.*
Lowe et al. Nucleic acid research, 1990, vol. 18(7), p. 1757-1761.*
Attached nucleic acid sequence search report.*
Buhler, Stephane, et al., 2009, "High levels of molecular polymorphism at the KIR2DL4 locus in French and Congolese populations: Impact for anthropology and clinical studies"; Human Immunology, 70:9;53-959.
Binladen, Jonas, et al., 2007, "The Use of Coded PCR Primers Enables High-Throughput Sequencing of Multiple Homolog Amplification Products by 454 Parallel Sequencing", PLOS One, Public Library of Science, 2(2).e197.1-e197.9.
Houtchens, Kathleen A., et al., 2007, "High-throughput killer cell immunoglobulin-like receptor genotyping of MALDI-TOF mass spectrometry with discovery of novel alleles", Immunogenetics, 59:525-537.
Ladner, Martha B., et al., 2009, "190-P: High-resolution KIR genotyping on pooled samples by next generation sequencing", Human Immunology, 70(1):S107.
Margulies, Marcel, et al., 2005, "Genome sequencing in microfabricated high-densisty picolitre reactors", Nature, 437(7057):376-380.
Jiang, Kan, et al., 2005, "The establishment of PCR-SSP method for killer cell immunoglobulin-like receptor gene family and its application", Chinese Journal of Microbiology and Immunology, 25(12):1044-1048.
Zhang, Lei, et al., 2003, "Killer Ig-like receptor gene content diversity and haplotype analysis in Chinese Han population in Shanghai", Chinese Journal of Medical Genetics, 20(5):396-399.
Bentley, Gordon, et al., 2009, "High-resolution, high-throughput HLA genotyping by next-generation sequencing", Tissue Antigens, 74:393-403.
Cooley, Sarah, et al., 2009, "Donors with group B KIR haplotypes improve relapse-free survival after unrelated hematopoietic cell transplantation for acute myelogenous leukemia", Blood, 113(3):726-732.
Hoffmann, Christian, et al., 2007, "DNA bar coding and pyrosequencing to identify rare HIV drug resistance mutations", Nucleic Acids Research, 35(13):e91.
Hollenbach, Jill A., et al., 2009, "Susceptibility to Crohn's disease is mediated by KIR2DL2/KIR2DL3 heterozygosity and the HLA-C ligand", Immunogenetics, 61:663-671.
Lanier, Lewis L., et al., 1995, "The NKB1 and HP-3E4 NK Cell Receptors are Structurally Distinct Glycoproteins and Independently Recognize Polymorphic HLA-B and HLA-C Molecules", The Journal of Immunology, 154:3320-3327.
Litwin, Virginia, et al., 1994, "NKB1: A Natural Killer Cell Receptor Involved in the Recognition of Polymorphic HLA-B Molecules", The Journal of Experimental Medicine, 180:537-543.
Miller, Jeffery S., et al., 2007, "Missing KIR ligands are associated with less relapse and increased graft-versus-host disease (GVHD) following unrelated donor allogeneic HCT", Blood, 109(11):5058-5061.

(Continued)

*Primary Examiner* — Kenneth R. Horlick
*Assistant Examiner* — Joyce Tung
(74) *Attorney, Agent, or Firm* — Olga Kay

(57) ABSTRACT

Disclosed is a method of determining KIR genotypes for one or more individuals in parallel, the method comprising: for each individual, amplifying the polymorphic exon sequences of the KIR genes, pooling the KIR amplicons, performing emulsion PCR followed by pyrosequencing in parallel to determine all the amplicon sequences present in the individual to determine which KIR alleles are present in the individual.

12 Claims, 11 Drawing Sheets

(56) References Cited

OTHER PUBLICATIONS

Martin, M. P., et al., 2008, "KIR haplotypes defined by segregation analysis in 59 Centre d'Etude Polymorphisime Humain (CEPH) families", Immunogenetics, 60:767-774.

Parameswaran, Poornima, et al., "A pyrosequencing-tailored nucleotide barcode design unveils opportunities for large-scale sample multiplexing", Nucleic Acid Research, 35(19):e130, 2007.

Parham, Peter, 2005, "MHC Class I Molecules and KIRS in Human History, Health and Survival", Nature Reviews: Immunology, 5:201-214.

Parham, Peter, et al., 2003, "Alloreactive Killer Cells: Hindrance and Help for Haematopoietic Transplants", Nature Reviews: Immunology, 3:108-122.

Thomas, Roman K., 2006, "Sensitive mutation detection in heterogeneous cancer specimens by massively prallel picoliter reactor sequencing", Nature Medicine, 12(7):852-855.

Cooley, Sarah, et al. 2009, "Donors with Group B KIR Haplotypes Improve Relapse-Free Survival After Unrelated Hematopoietic Cell Transplantation for Acute Myelogenous Leukemia", Blood, 113(3): 726.

* cited by examiner

Martin MP, et al., *Immunogenetics*. 2008 Dec;60(12):767-774.

FIGURE 2

Parham P, et al. *Nature Rev Immunology.* 2003;3:108-122.

| RECEPTOR | LIGAND |
|----------|--------|
| KIR2DL1  | HLA-Cw2 |
| KIR2DL2  | HLA-Cw1 |
| KIR2DL3  | HLA-Cw1 |
| *KIR2DS1* | |
| *KIR2DS2* | |
| *KIR2DS3* | |
| *KIR2DS4* | |
| *KIR2DS5* | |
| KIR2DL4  | HLA-G |
| KIR2DL5  | |
| KIR3DL1  | HLA-Bw4 |
| KIR3DL2  | HLA-A |
| KIR3DL3  | |
| *KIR3DS1* | |

GTCTATATGAGAAACCTTCTCTCTCAGCCCAGCGGGGCCCCACGGTTCTGGCAGGAGAGAATGTGACCTTGTCCTGCAGCTCCC
GGAGCTCCTATGACATGTACCATCTATCCAGGAAGGGGAGGCCCATGAACGTAGGCTCCCTGCA

2DL2

GTCTATATGAGAAACCTTCTCTCTCAGCCCAGCCGGGGCCCCACGGTTCTGGCAGGAGAGAGGGTGACCTTGTCCTGCAGCTCCC
GGAGCTCCTATGACATGTACCATCTATCCAGGAGGGGAGGCCCATGAA?GTAGGTTCTCTGCA

2DL3

GTCTATATGAGAAACCTTCTCTCTCAGCCCAGCCGGGGCCCCACGGTTCTGGCAGGAGAGAGGGTGACCTTGTCCTGCAGCTCCC
GGAGCTCCTATGACATGTACCATCTATCCAGGAGGGGAGGCCCATGAACGTAGGTTCTCTGCA

2DL4

GTCTATATGAGAAACCTTCGCTTACAGCCCGGCGGGGCCCCACGGTTCGCACAGGAGAGAACGTGACCTTGTCCTGCAGCTCCC
AGAGCTCCTTTGACATCTACCATCTATCCAGGAAGGGGAAGCCCATGAACTTAGGCTCCCTGCA

GTCTATTTGGGAAACCTTCACTCTCTCAGCCCAGCCCGGGCCCCACGGTTCGCACAGGAGAGAACGTGACCTTGTCCTGCAGCTCCA
GGAGCTCATTTGACACATGTACCATCTATCCAGGGAGGGCCCATGAACCTAGGCTCCCTGCA

2DS1

GTCTATATGAGAAACCTTCTCTCTCAGCCCAGCCCGGGCCCCACGGTTCTGGCAGGAGAGAATGTGACCTTGTCCTGCAGCTCCC
GGAGCTCCTATGACATGTACCATCTATCCAGGGAAGGGAGGCCCATGAACGTAGGCTCCCTGCA

2DS2

GTCTATATGAGAAACCTTCTCTCTCAGCCCAGCCCGGGCCCCACGGTTTTGGCAGGAGAGAGGCGTGACCTTGTCCTGCAGCTCCC
GGAGCTCCTATGACATGTACCATCTATCCAGGGAGGGCCCATGAACGTAGGTTCTCTGCA

2DS3

GTCTATATGAGAAACCTTCTCTCTCAGCCCAGCCCGGGCCCCACGGTTCTGGCAGGAGAGAGGCGTGACCTTGTCCTGCAGCTCCT
GGAGCTCCTATGACATGTACCATCTATCCACGGAGGGGAGGCCCATGAACGTAGGTTCTCTGCA

GTCTATATGAGAAACCTTCTCTCTCAGCCCAGCCGGGGCCCACGGTTCAGGCAGGAGAGAATGTGACCTTGTCCTGCAGCTCCC
GAGCTCCTATGACATGTACCATCTATCCAGGAAGGGGAGGCCCATGAACGTAGGCTCCCTGCA

2DS5

GTCTATATGAGAAACCTTCTCTCTCCCAGCCCAGCCGGGGCCCCACGGTTCTGGCAGGAGAGAGGTGACCTTGTCCTGCAGCTCCC
GGAGCTCCTATGACATGTACCATCTATCCAGGAAGGGGAGGCCCATGAACGTAGGCTCCCTGCA

3DL1

GTCCATATGAGAAACCTTCTCTCTCAGCCCAGCCGGGGCCCAAGGTTCAGGCAGGAGAGCGTGACCTTGTCCTGTAGCTCCC
GGAGCTCCTATGACATGTACCATCTATCCAGGAGGGGGAGCCCATGAACGTAGGCTCCCTGCA

3DL2

GTCTATATGAGAAACCTTCTCTCTCAGCCCAGCCGGGGCCCCACGGTTCAGGCAGGAGAACGTGACCTTGTCCTGTAGCTCCT
GGAGCTCCTATGACATCTACCATCTGTCCAGGGAAGGGAGGCCCATGAACGTAGGCTCCGTGCA

GTCTATATGGGAAACCTTCTCTCTCAGCCCAGCCGGGCCCCACGGTTCAGGCAGGAGAGAATGTGACCTTGTCCTGCAGCTCC

GGAGCTTGTTTGACATTTACCATCTATCCAGGGAGGCAGAGGCCGGTGAACTTAGGCTCACTGCG

3DS1

GTCTATATGAGAAACCTTCTCTCTCAGCCCCAGCCGGGGCCCCAAGGTTCAGGCAGGAGAGAGGGTGACCTTGTCCTGTAGCTCCC

GGAGCTCCTATGACATGTACCATCTATCCAGGGAGGGGGAGCCCATGAACGTAGGCTCCCTGCA

2DP1

GTCTATATGAGAAACCTTCTCTCTCAGCCCAGCCGGGCCCCACGGTTCTGGCAGGAGAGAGGGTGACCTTGTCCTGCAGCTCCC

GGAGCTCCTATGACATGTACCATCTATCCACGGAGGGGAGGCCCATGAACGTAGGTTCTCTGCA

3DP1

GTCTATGTGGAAACCTTCTCTCTCAGCCCAGCCGGGCCCCCATGGTTAAGGCAGGAGAGGCGTGACCTTGTCCTGCAGCTCCC

GGAGCTCCTATGACATCTACCATCTATCAAGGGACGGGGAGGCTCATGAACTTAGGTTCCCTGCA

FIGURE 4

2DL1
GGGCCAAGGTCAACGGAACATTCCAGGGTGACTTTCCTCTGGGCCCTGCCACCCACGGAGGGACCTACAGATGCTTCGGCTCT
TTCCATGACTCTCCATACGAGTGGTCAAAGTCAAAGTGACCCACTGCTTGTTCTGTCACAG

2DL2
GGGCCCAAGGTCAACGGAACATTCCAGGGCCGACTTTCCTCTGGCCCCTGCCACCCACGGAGGAACCTACAGATGCTTCGGCTCT
TTCCGTGACTCTCCATACGAGTGGTCAAACTCGAGTGACCCACTGCTTGTTCTGTCATAG

2DL3
GGGGCCCAAGGTCAACGGAACATTCCAGGGCCGACTTTCCTCTGGGCCCTGCCACCCACGGAGGAACCTACAGATGCTTCGGCTCT
TTCCGTGACTCTCCATACGAGTGGTCAAACTCGAGTGACCCACGCTTGTTCTGTCACAG

2DL4
GTGCCCAGCATCAATGGAACATTCCAGGCCGACTTCCCTGGGTCTGCCACCCACGGAGAGACCTACAGATGCTTCGGCTCT
TTCCATGGATCTCCCTACGAATGGTCAGACGGGAGTGACCCACTGCCTGTTTCTGTCACAG

GTGCCCAGGCGTCAATGGAACATTCCAGGCTGACTTTCCTCTGGGCCCTGCCACCACGGAGGGACCTACACATGCTTCGGCTCT
CTCCATGACTCACCCTATGAGTGGTCAGACCCGAGTGACCCACTGCTGTTCTGTCACAG

2DS1

GGGACCAAGGTCAACGGAACATTCCAGGCCAACTTTCCTCTGCGGGCCCTGCCACCCATGGAGGGACCTACAGATGCTTCGGCTCT
TTCCGTGACTCTCCATACGAGTGGTCAAAGTCAAGTGACCCACTGCTGTTTCTGTCACAG

2DS2

GGGCCCAAGGTCAACGGAACATTCCAGGCCGACTTTCCTCTGGGCCCTGCCACCACGGAGGAACCTACAGATGCTTCGGCTCT
TTCGGTGACTCTCCCTATGAGTGGTCAAACTCGAGTGACCCACTGCTTGTTTCTGTCACAG

GGGCCCAAGGTCAAGGAACATTCCAGGCCGACTTTCCCTCTGGGCCCTGCCACCCAAGGAGGAACCTACAGATGCTTCGGCTCT
TTCCATGACTCTCCCTACGAGTGGTCAAAGTCAAGTGACCCACTGCTTGTTCTGTCACAG

2DS4

GTGCGGCAGCATCAACGGAACATTCCAGGCCGACTTTCGTCTGGGCCCTGCCACCCACGGAGGACCTACAGATGCTTGGGCTCT
TTCCGTGACGCTCCCTACGAGTGGTCAAACTGAGTGATCCACTGCTTGTTCCGTCACAG

2DS5

GGGCCCAAGGTCAACAGAACATTCCAGGCCGACTCTCCTCTGGACCCTGCCACCCACGGAGGGCCTACAGATGCTTCGGCTCT
TTCCGTGACTCTCCATACGAGTGGTCAAAGTCAAGTGACCCACTGCTTGTTTCTGTCACAG

3DL1

GTGCGGCAAGGTCAACAGAACATTCCAGGCAGATTCCCTCTGGGCCCTGCCACCCACGGAGGGACCTACAGATGCTTCGGCTCT
TTCCGTCACTCTCCCTACGAGTGGTCAGACCCGAGTGACCCACTGCTTGTTTCTGTCACAG

GTGCCCAAGGTCAACAGAACATTCCAGGCAGACTTTCCTCTGGGCCCTGCCACCCACGGAGGAGGACCTACAGATGCTTCGGCTCT
TTCCGTGCCCTGCCCTGCGTGTGGTCAAACTCAAGTGACCCACTGCTTGTTTCTGTCACAG

3DL3

GTGCTGAGGGTCAATGGAACATTCCAGGCCAACTTCCCTCTGGGCCCTGTGACCCACGGAGGAACTACAGATGCTTCGGCTCT
TTCCGTGCCCTGCCCACGCGTGGTCAGACCCGAGTGACCCACTGCCCGTTCTGTCACAG

3DS1

GTGCGCAAGGTCAACAGAACATTCCAGGCAGATTCCCTCTGGGCCCTGCCACCCACGGAGGACCTACAGATGCTTCGGCTCT
TTCCGTCACTCTCCCTACGAGTGGTCAGACCCGAGTGACCCACTGCTTGTTTCTGTCACAG

2DP1

GGGCCAAGGTCAACGGAACATTCCAGGCTGACTTTCCTCTGGGCCCTGCCACCCACGGAGGAACCTACAGATGCTTCGGCTCT
TTCCGTGACTCTCCCTACGAGTGGTCAAACTGGACCCACTGCTTGTTTCTGTCACAG

GTGCCAAGGTCAATGGAACCTTCCAGGCCAACTTTCCTCTGGCCCTGCCACCACGGAGGACCTACAGATGCTTCGGCTCT
TTCCGTGACTCTCCCTACGAGTGGTCAGACCTTAGTGACCCACTGCTGTTTCTGTCACAG

DETERMINATION OF KIR HAPLOTYPES ASSOCIATED WITH DISEASE

PRIORITY CLAIM

This application claims priority to a U.S. application Ser. No. 61/244,821, filed on Sep. 22, 2009.

FIELD OF THE INVENTION

The invention relates to the methods of molecular diagnostics and more specifically, determining genotypes of individuals where particular genotypes are known to be associated with disease.

BACKGROUND OF THE INVENTION

The present invention is a method of determining the sequences of natural killer cell immunoglobulin-like receptor or "KIR" genes within a single individual or within each one of simultaneously tested multiple individuals.

Natural Killer Cells

Natural Killer (NK) cells are part of the innate immune system and are specialized for early defense against infection as well as tumors. The NK cells were first discovered as a result of their ability to kill tumor cell targets. Unlike cytolytic T-cells, NK cells can kill targets in a non-major histocompatibility complex (non-MHC)-restricted manner. As an important part of the innate immune system, the NK cells comprise about 10% of the total circulating lymphocytes in the human body.

Because of their ability to kill other cells, NK cells are normally kept under tight control. All normal cells in the body express the MHC class I molecules on their surface. These molecules protect normal cells from killing by the NK cells because they serve as ligands for many of the receptors found on NK cells. Cells lacking sufficient MHC class I on their surface are recognized as 'abnormal' by NK cells and killed. Simultaneously with killing the abnormal cells, the NK cells also elicit a cytokine response.

Natural killer cells constitute a rapid-response force against cancer and viral infections. These specialized white blood cells originate in the bone marrow, circulate in the blood, and concentrate in the spleen and other lymphoid tissues. NK cells key their activities on a subset of the human leukocyte antigen (HLA) proteins that occur on the surfaces of healthy cells but that virus- and cancer-weakened cells shed. The HLA proteins are encoded by Major Histocompatibility Complex (MHC) genes. When NK cells encounter cells that lack HLA proteins, they attack and destroy them—thus preventing the cells from further spreading the virus or cancer. NK cells are distinguished from other immune system cells by the promptness and breadth of their protective response. Other white blood cells come into play more slowly and target specific pathogens—cancers, viruses, or bacteria—rather than damaged cells in general.

KIR genes

The natural killer cell immunoglobulin-like receptor (KIR) gene family is one of several families of receptors that encode important proteins found on the surface of natural killer (NK) cells. A subset of the KIR genes, namely the inhibitory KIR, interact with the HLA class I molecules, which are encoded within the human MHC. Such interactions allow communication between the NK cells and other cells of the body, including normal, virally infected, or cancerous cells. This communication between KIR molecules on the NK cells and HLA class I molecules on all other cells, helps determine whether or not cells in the body are recognized by the NK cells as self or non-self. Cells which are deemed to be 'non-self' are targeted for killing by the NK cells.

KIR Gene and Protein Structure

The KIR gene family consists of 16 genes (KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1/S1, KIR3DL2, KIR3DL3, KIR2DP1 and KIR3DP1.) The KIR gene cluster is located within a 100-200 kb region of the Leukocyte Receptor Complex (LRC) located on chromosome 19 (19q13.4) The gene complex is thought to have arisen by gene duplication events occurring after the evolutionary split between mammals and rodents The KIR genes are arranged in a head-to tail fashion, with only 2.4 kb of sequence separating the genes, except for one 14 kb sequence between 3DP1 and 2DL4. Because the KIR genes arose by gene duplication, they are very similar in sequence, showing 90-95% identity with one another. Human individuals differ in the number and type of KIR genes that they inherit; the KIR genotype of individuals and within ethnic groups can be quite different. At the chromosomal level, there are two distinct types of KIR haplotypes (See FIG. 1, adapted from Martin et al. *Immunogenetics*. (2008) December; 60(12):767-774). The A-haplotype contains no stimulatory genes (2DS and 3DS1) other than 2DS4, no 2DL5 genes and no 2DL2 genes. The B-haplotype is more variable in gene content, with different B-haplotypes containing different numbers of stimulatory genes, either one or two 2DL5 genes, etc. (Martin M P, et al. (2008) KIR haplotypes defined by segregation analysis in 59 Centre d'Etude Polymorphisme Humain (CEPH) families. *Immunogenetics*, December; 60(12):767-774.).

All of the KIR proteins are anchored to the cell membrane, with either two or three extracellular immunoglobulin-like domains and a cytoplasmic tail. Nine KIR genes (KIR2DL and KIR3DL) encode proteins with long cytoplasmic tails that contain immune tyrosine-based inhibitory motifs (ITIM). These KIR proteins can send inhibitory signals to the natural killer cell when the extra-cellular domain has come into contact with its ligand. The remaining KIR genes encode proteins with short cytoplasmic tails. These proteins send activating signals via adaptor molecules like DAP12.

KIR receptor structure and the identity of the HLA class I ligands for each KIR receptor are shown on FIG. 2 (adapted from Parham P. et al., Alloreactive killer cells: hindrance and help for hematopoietic transplants. *Nature Rev. Immunology*. (2003)3:108-122.) The nomenclature for the killer-cell immunoglobulin-like receptors (KIRs) describes the number of extracellular immunoglobulin-like domains (2D or 3D) and the length of the cytoplasmic tail (L for long, S for short). Each immunoglobulin-like domain is depicted as a loop, each immunoreceptor tyrosine-based inhibitory motif (ITIM) in the cytoplasmic tail as an oblong shape, and each positively charged residue in the transmembrane region as a diamond. The stimulatory KIR are noted in italics. (Parham P. et al., (2003).

The strength of the interactions between the KIR and their HLA class I ligands can be dependent upon both the KIR sequence and the HLA sequence. While the HLA region has been studied for over 40 years, the KIR molecules were first described (as NKB1) in the mid-1990s (Lanier et al. (1995) The NKB1 and HP-3E4 NK cells receptors are structurally distinct glycoproteins and independently recognize polymorphic HLA-B and HLA-C molecules. *J. Immunol*. April 1; 154(7):3320-3327 and Litwin V. et al. (1994) NKB1: a natural killer cell receptor involved in the recognition of polymorphic HLA-B molecules. *J Exp Med*. August 1; 180(2):537-543).

The first years of discovery were mainly devoted to describing the different KIR genes, and methods were developed to determine individual KIR genotypes. Utilizing these methods, KIR gene associations with autoimmune disease and recipient survival after allogeneic hematopoietic cell transplantation have been shown (Parham P. (2005) MHC class I molecules and KIRs in human history, health and survival. *Nature reviews*, March; 5(3):201-214). It is now clear that each KIR gene has more than one sequence; that is, each KIR gene has variable sequence because of single nucleotide polymorphisms (SNPs), and in some instances, insertions or deletions within the coding sequence. Studies have shown that KIR3DL1 polymorphism can affect not only the expression levels of KIR3DL1 on natural killer cells, but also the binding affinity of KIR3DL1 to its ligand.

KIR Association with Disease

Studies designed to investigate the role of KIR in human disease have shown an association with various KIR genes and viral infections such as CMV, HCV and HIV, autoimmune diseases, cancer and preeclampsia (Parham P. (2005) MHC class I molecules and KIRs in human history, health and survival. *Nature reviews*, March; 5(3):201-214). In a recent study on genetic susceptibility to Crohn's disease, an inflammatory autoimmune bowel disease, it was found that patients who are heterozygous for KIR2DL2 and KIR2DL3 and homozygous for the C2 ligand are susceptible to disease, whereas the C1 ligand is protective. (Hollenbach J A et al. (2009) Susceptibility to Crohn's Disease is mediated by KIR2DL2/KIR2DL3 heterozygosity and the HLAC ligand. *Immunogenetics*. October; 61(10):663-71). Other studies on KIR and unrelated hematopoietic cell transplantation (HCT) for Acute Myeloid Leukemia (AML) have shown a significantly higher 3 year overall survival rate and a 30% overall improvement in the risk of relapse-free survival with B/x donors compared to A/A donors. (Cooley S, et al. (2009) Donors with group B KIR haplotypes improve relapse-free survival after unrelated hematopoietic cell transplantation for acute myelogenous leukemia. *Blood*. January 15; 113(3): 726-732; and Miller J S, et al. (2007) Missing KIR-ligands is associated with less relapse and increased graft versus host disease (GVHD) following unrelated donor allogeneic HCT. *Blood*, 109(11):5058-5061). Such studies have been performed with knowledge of the KIR genotype of patients and controls, but have not been performed for KIR at an allelic level. Much as specific HLA alleles have been shown to be important in human disease, (for example HLA-DR3 and HLA-DR4 association with type I diabetes and HLA-DR8 with juvenile rheumatoid arthritis) the ability to genotype KIR at the allelic level will refine studies associating KIR with human disease.

SUMMARY OF THE INVENTION

The invention is a method of determining KIR genotypes for one or more individuals in parallel, the method comprising: for each individual, performing an amplification reaction with a forward primer and a reverse primer, each primer comprising an adapter sequence, an individual identification sequence, and a KIR-hybridizing sequence, to amplify the exon sequences of the KIR genes that comprise polymorphic sites to obtain KIR amplicons; pooling KIR amplicons from more than one individual obtained in the first step; performing emulsion PCR; determining the sequence of each KIR amplicon for each individual using pyrosequencing in parallel; and assigning the KIR alleles to each individual by comparing the sequence of the KIR amplicons determined in the pervious step to known KIR sequences to determine which KIR alleles are present in the individual.

In other embodiments the method further comprises a step of determining that the individual is predisposed to preeclampsia or autoimmune disease or that the individual is a suitable unrelated hematopoietic stem cell donor when certain KIR alleles have been found in the individual.

In other embodiments, the method further comprises a step of determining the individual's HLA genotype. In yet other embodiments, after the step of determining the individual's HLA genotype, the method further comprises a step of determining that the individual is predisposed to clearing an HCV infection, slow progression of HIV infection to AIDS or Crohn's disease when certain KIR alleles in combination with certain HLA alleles have been found in the individual In other embodiments, the invention is a reaction mixture for obtaining KIR amplicons to determine KIR genotypes in one or more individuals in parallel, comprising a set of primers which includes: a forward primer comprising an adapter region, an individual identification tag and a KIR-hybridizing region; and a reverse primer that comprises an adapter region, an individual identification tag, and a KIR-hybridizing region.

In other embodiments, the invention is a kit for obtaining KIR amplicons to determine KIR genotypes in one or more individuals in parallel, comprising: a forward primer comprising an adapter region, an individual identification tag and a KIR-hybridizing region; a reverse primer that comprises an adapter region, an individual identification tag, and a KIR-hybridizing region.

BRIEF DESCRIPTION OF THE DRAWINGS

FIG. 2 is a schematic representation of structures of the KIR receptors and the identity of their HLA class I ligands.

FIG. 3 illustrates a nucleotide alignment across the sequence of the first half of exon 5 of all KIR genes.

FIG. 4 illustrates a nucleotide alignment across the sequence of the second half of exon 5 of all KIR genes.

DETAILED DESCRIPTION OF THE INVENTION

I. Definitions

Figure 1:
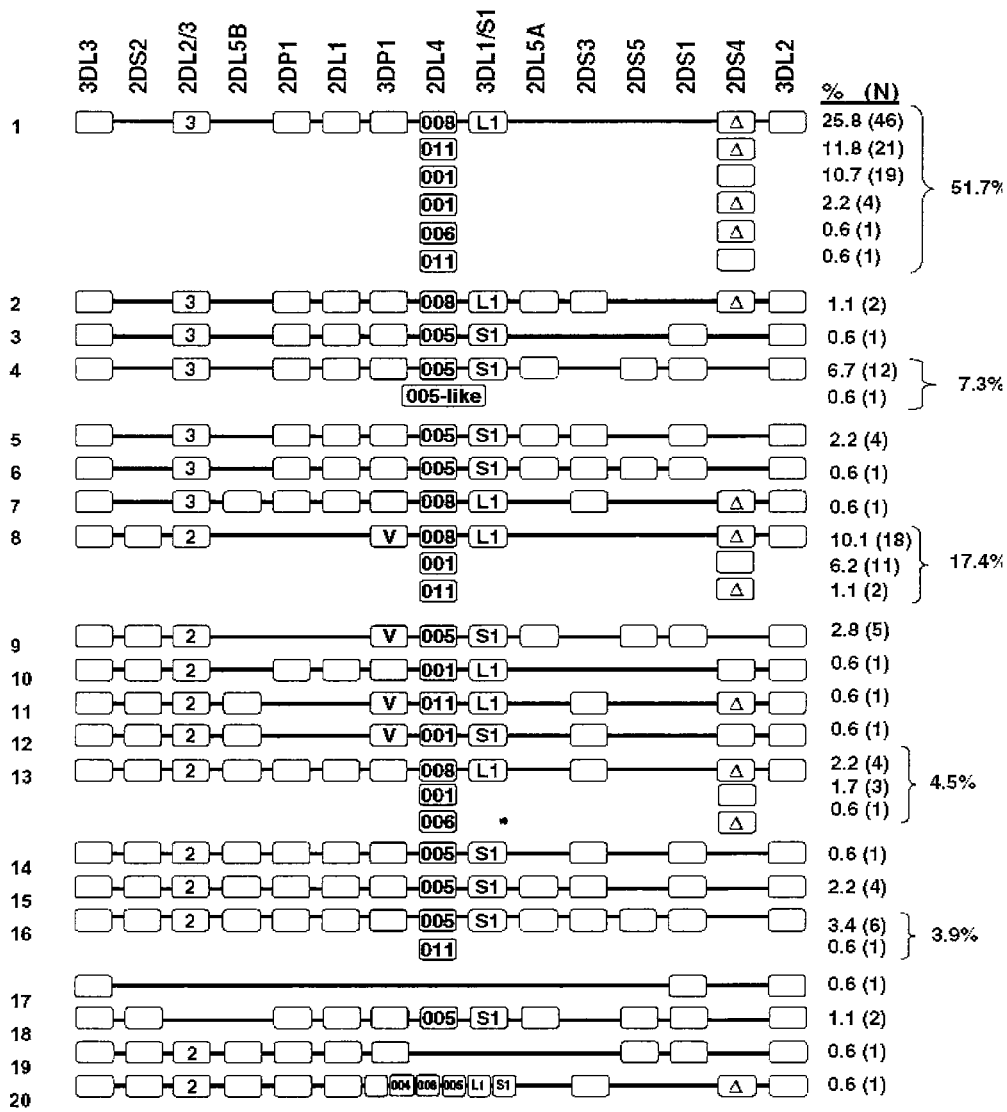
FIG. 1 is a schematic representation of the KIR haplotypes.

The term "allele" refers to a sequence variant of a gene. At least one genetic difference can constitute an allele. For KIR genes, multiple genetic differences typically constitute an allele.

The term "amplicon" refers to a nucleic acid molecule that contains all or fragment of the target nucleic acid sequence and that is formed as the product of in vitro amplification by any suitable amplification method.

The term "polymorphism" refers to the condition in which two or more variants of a specific nucleotide sequence, or the encoded amino acid sequence, can be found in a population. A polymorphic position refers to a site in the nucleic acid where the polymorphic nucleotide that distinguishes the variants occurs. A "single nucleotide polymorphism" or SNP, refers to a polymorphic site consisting of a single nucleotide.

The term "haplotype" refers to a combination of alleles at different places (loci or genes) on the same chromosome in an individual.

The term "genotype" with respect to a particular gene refers to a sum of the alleles of the gene contained in an individual or a sample.

The terms "determining the genotype" of a KIR gene refers to determining the polymorphisms present in the individual alleles of the KIR gene present in a subject.

The terms "target region" or "target sequence" refer to a polynucleotide sequence to be studied in a sample. In the context of the present invention, the target sequences are the KIR gene sequences contained in the sample from an individual.

The term "oligonucleotide" refers to a short nucleic acid, typically ten or more nucleotides in length. Oligonucleotides are prepared by any suitable method known in the art, for example, direct chemical synthesis as described in Narang et al. (1979) *Meth. Enzymol.* 68:90-99; Brown et al. (1979) *Meth. Enzymol.* 68:109-151; Beaucage et al. (1981) *Tetrahedron Lett.* 22:1859-1862; Matteucci et al. (1981) *J. Am. Chem. Soc.* 103:3185-3191; or any other method known in the art.

The term "primer" refers to an oligonucleotide, which is capable of acting as a point of initiation of nucleic acid synthesis along a complementary strand of a template nucleic acid. A primer that is at least partially complementary to a subsequence of a template nucleic acid is typically sufficient to hybridize with template nucleic acid and for extension to occur. Although other primer lengths are optionally utilized, primers typically comprise hybridizing regions that range from about 6 to about 100 nucleotides in length and most commonly between 15 and 35 nucleotides in length. The design of suitable primers for the amplification of a given target sequence is well known in the art and described in the literature cited herein. The design of suitable primers for parallel clonal amplification and sequencing is described e.g. in a U.S. Application Pub. No. 20100086914.

A "thermostable nucleic acid polymerase" or "thermostable polymerase" is a polymerase enzyme, which is relatively stable at elevated temperatures when compared, for example, to polymerases from *E. coli*. As used herein, a thermostable polymerase is suitable for use under temperature cycling conditions typical of the polymerase chain reaction ("PCR").

The term "adapter region" of a primer refers to the region of a primer sequence at the 5' end that is universal to the KIR amplicons obtained in the method of the present invention and provides sequences that anneal to an oligonucleotide present on a microparticle (i.e. bead) or other solid surface for emulsion PCR. The adapter region can further serve as a site to which a sequencing primer binds. The adapter region is typically from 15 to 30 nucleotides in length.

The terms "library key tag" refer to the portion of an adapter region within a primer sequence that serves to differentiate a KIR-specific primer from a control primer.

The terms "multiplex identification tag", "individual identification tag" or "MID" are used interchangeably to refer to a nucleotide sequence present in a primer that serves as a marker of the DNA obtained from a particular subject or sample.

The terms "nucleic acid" refers to polymers of nucleotides (e.g., ribonucleotides and deoxyribonucleotides, both natural and non-natural) such polymers being DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non-natural bases. The example of non-natural bases include those described in, e.g., Seela et al. (1999) *Helv. Chim. Acta* 82:1640. Certain bases used in nucleotide analogs act as melting temperature ($T_m$) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

The terms "natural nucleotide" refer to purine- and pyrimidine-containing nucleotides naturally found in cellular DNA and RNA: cytosine (C), adenine (A), guanine (G), thymine (T) and uracil (U).

The term "non-natural nucleotide" or "modified nucleotide" refers to a nucleotide that contains a modified base, sugar or phosphate group, or that incorporates a non-natural moiety in its structure. The non-natural nucleotide can be produced by a chemical modification of the nucleotide either as part of the nucleic acid polymer or prior to the incorporation of the modified nucleotide into the nucleic acid polymer. In another approach a non-natural nucleotide can be produced by incorporating a modified nucleoside triphosphate into the polymer chain during enzymatic or chemical synthesis of the nucleic acid. Examples of non-natural nucleotides include dideoxynucleotides, biotinylated, aminated, deaminated, alkylated, benzylated and fluorophor-labeled nucleotides.

The term "nucleic acid polymerases" or simply "polymerases" refers to enzymes, for example, DNA polymerases, that catalyze the incorporation of nucleotides into a nucleic acid. Exemplary thermostable DNA polymerases include those from *Thermus thermophilus, Thermus caldophilus, Thermus* sp. ZO5 (see, e.g., U.S. Pat. No. 5,674,738) and mutants of the *Thermus* sp. ZO5 polymerase (see, e.g. U.S. patent application Ser. No. 11/873,896, filed on Oct. 17, 2007), *Thermus aquaticus, Thermus flavus, Thermus filiformis, Thermus* sp. sps17, *Deinococcus radiodurans*, Hot Spring family B/clone 7, *Bacillus stearothermophilus, Bacillus caldotenax, Escherichia coli, Thermotoga maritima, Thermotoga neapolitana* and *Thermosipho africanus*. The full nucleic acid and amino acid sequences for numerous thermostable DNA polymerases are available in the public databases.

The terms "polymerase chain reaction amplification conditions" or "PCR conditions" refer to conditions under which primers that hybridize to a template nucleic acid are extended by a polymerase during a polymerase chain reaction (PCR). Those of skill in the art will appreciate that such conditions can vary, and are generally influenced by the nature of the primers and the template. Various PCR conditions are described in *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990)."

The term "sample" refers to any composition containing or presumed to contain nucleic acid from an individual. The sample can be obtained by any means known to those of skill in the art. Such sample can be an amount of tissue or fluid, or a purified fraction thereof, isolated from an individual or individuals, including tissue or fluid, for example, skin, plasma, serum, whole blood and blood components, spinal fluid, saliva, peritoneal fluid, lymphatic fluid, aqueous or vitreous humor, synovial fluid, urine, tears, seminal fluid, vaginal fluids, pulmonary effusion, serosal fluid, organs, bronchio-alveolar lavage, tumors and paraffin embedded tissues. Samples also may include constituents and components of in vitro cultures of cells obtained from an individual, including, but not limited to, conditioned medium resulting from the growth of cells in the cell culture medium, recombinant cells and cell components.

II. Introduction

While a large group of KIR gene alleles has been described by methods in which individual KIR genes are sequenced one at a time (Table 1: 335 alleles), no methods have been developed which can determine all the KIR alleles present in patient samples in a time efficient manner.

TABLE 1

The number of KIR Polymorphisms identified to date.

| KIR Gene | 2DL1 | 2DL2 | 2DL3 | 2DL4 | 2DL5 | 2DS1 | 2DS2 | 2DS3 |
|---|---|---|---|---|---|---|---|---|
| Alleles | 25 | 11 | 9 | 25 | 21 | 12 | 12 | 9 |
| Proteins | 18 | 7 | 8 | 12 | 11 | 8 | 6 | 3 |
| Nulls | 1 | 0 | 1 | 0 | 0 | 0 | 0 | |

| KIR Gene | 2DS4 | 2DS5 | 3DL1 | 3DS1 | 3DL2 | 3DL3 | 2DP1 | 3DP1 |
|---|---|---|---|---|---|---|---|---|
| Alleles | 20 | 12 | 52 | 14 | 45 | 55 | 5 | 8 |
| Proteins | 13 | 9 | 46 | 12 | 40 | 31 | 0 | 0 |
| Nulls | | 0 | 1 | 1 | 0 | 0 | 0 | 0 |

The present invention provides methods of KIR genotyping based the discovery that a multiplex, parallel clonal sequencing analysis can be used to genotype at least one exon in all 16 KIR genes in multiple individuals at the same time. Next-generation sequencing methods referred to as "highly multiplexed amplicon sequencing" are able to clonally propagate in parallel millions of nucleic acid molecules which are then also sequenced in parallel. Recently, the read lengths obtainable by such next-generation sequencing methods have increased to >400 nucleotides using Titanium chemistry. These clonal read lengths make possible setting the phase of the linked polymorphisms within an exon of a KIR gene and thus identifying each allele of each of the KIR genes. In the current invention, the system is sufficiently high throughput to enable typing each of the 9 exons (each with multiple polymorphisms) of each of the 16 KIR genes for up to 10 individuals in a single sequencing run.

The method of the present invention utilizes the high-throughput sequencing technology able to generate long reads. Especially advantageous is the use of highly multiplexed amplicon sequencing that utilizes the pyrosequencing technology. This technology is based on detecting base incorporation by the release of a pyrophosphate and simultaneous enzymatic nucleotide degradation as described, e.g., in U.S. Pat. Nos. 6,274,320, 6,258,568 and 6,210,891. In some embodiments, the technology involves the use of emulsion PCR (emPCR™) as described in detail in U.S. Patent Application Pub. No. 20100086914.

One of the technical challenges for KIR typing is the difficulty in setting phase for the many linked polymorphisms. The present invention solves the problem of phase ambiguity by the use of clonal sequencing. Clonally obtained, long sequencing reactions are uniquely able to link a 'KIR gene signature motif' to the longer sequences containing the polymorphic sites and differentiate the particular KIR allele from other KIR sequences. The longer the sequence obtained from a clonal sequencing reaction, the easier it becomes to identify sequences belonging to each KIR gene. Next generation sequencing provides an order of magnitude increase in the number of reads of contiguous sequence obtainable in a short time. Most platforms for clonal sequencing achieve read lengths of only 25-60 base pairs (bp) in paired-end sequencing. Only the clonal pyrosequencing-based method developed by 454 Life Sciences (Branford, Conn.) and described in Margulies M. et al., (2005) (Genome sequencing in microfabricated high-density picoliter reactors. *Nature*. September 15; 437(7057):376-380) has achieved read lengths of >400 bp using the 454 GS FLX Titanium system (454 Life Sciences, Branford, Conn.).

II. Primers

In the method of the present invention, each sample from an individual is amplified at each KIR exon. The primers for use in the method of the present invention contain a KIR priming region (also referred to as KIR-specific region). The KIR-specific region hybridizes to the KIR sequence of interest, such as an exon, a portion of an exon, or an exon and portions of an intron. In some embodiments, the primers are specific for a single KIR gene, i.e. the primers specifically target for amplification an exon, or the polymorphic region of the exon of a single KIR gene. In other embodiments, the primers are generic for all KIR genes, i.e. able to hybridize to and support amplification of the same exon in all KIR genes. In some embodiments, the primers may contain portions of intronic sequence. In some instances, intronic sequence is useful in determining the identity of the KIR gene to which the sequence should be assigned. In some embodiments, a separate set of primers could be added to amplify exons of a KIR gene that has substantially different intronic sequence than all the other KIR genes, for example gene KIR2DL4.

For example, as shown in Table 2, in some embodiments, the primers targeting exons 1 and 2 of KIR genes are generic. In some embodiments, among the primers targeting exon 3 of the KIR genes, some primers are generic to all KIR genes, while other primers are generic to a subset of KIR genes, while some primers are gene-specific. The primers are selected such that each exon in each of the KIR genes tested is amplified with sufficient specificity to allow unambiguous determination of the KIR genotype from the sequence.

The primers employed in the amplification reaction include additional sequences: adapter sequences for emulsion PCR and an identifying sequence that serves as a marker for the DNA from a single individual. The description of functional elements such as tags and adaptors for primers used in clonal pyrosequencing can be found in U.S. patent application Ser. No. 10/767,894 (filed on Jan. 28, 2004), Ser. No. 12/156,242 (filed on May 29, 2008), Ser. No. 12/245,666 (filed on Oct. 3, 2008) and Ser. No. 12/380,139 (filed on Feb. 23, 2009).

The adapter portions of the primer sequences are present at the 5' end of the primers. The adapters serve as the site of annealing for the sequencing primers and also correspond to sequences present on solid support (such as beads) used in emulsion PCR, so that the amplicon can anneal to the solid support.

The primers for use in the methods of the present invention further comprise individual identifier tags or MID tags. The MID tags are present in the primers between the adapter region and the KIR priming region. These tags are used to mark the KIR amplicons from each individual who is being tested. As a result, all KIR amplicons obtained from the same, subject are marked with the same MID tag. The MID tags are also sequenced in the sequencing reaction.

The MID tags typically are at least 4 nucleotides in length, but longer MID tags, e.g., 6, 8, or 10 or more nucleotides in length are also useful. The use of such sequences is well know in the art. (see, Thomas, et al. (2006) *Nat. Med.*, 12:852-855; Parameswaran et al., (2007) *Nucl. Acids Res.*, 35:e130; and Hofmann et al., (2007) *Nucl. Acids Res.* 35:e91).

III. Amplification and Sequencing

The KIR amplicons may be obtained using any type of amplification reaction. In the present invention, the KIR amplicons are typically made by PCR using the primer pairs described above. It is typically desirable to use a "high-fidelity" nucleic acid polymerase, i.e. a polymerase with a low error rate, e.g., such as a high-fidelity Taq polymerase (Roche Diagnostics).

The amplifications for each subject to be genotyped are performed separately. The amplicons from the individual subject are then pooled for subsequent emulsion PCR and sequence analysis.

The resulting pools of KIR amplicons are attached to beads and subjected to emulsion PCR. Emulsion PCR is known in the art (see U.S. Application Pub. No. 20100086914 and references cited therein). In emulsion PCR, the template to be amplified, in this case a KIR amplicon, is attached to a solid support, preferably a spherical bead, via hybridization to a primer conjugated to said bead.

Following emulsion PCR amplification, the beads that have the amplicons are isolated. The amplicons are then sequenced using DNA sequencing technology that is based on the detection of base incorporation by the release of a pyrophosphate and simultaneous enzymatic nucleotide degradation (as described in U.S. Pat. Nos. 6,274,320, 6,258,568 and 6,210,891).

IV. Determining the Gene Sequence

Once the sequencing data of the individual DNA molecule is obtained, the unambiguous exon sequence is determined. For some known genes, such as HLA, the allele sequence can be established by comparing the sequence files to an HLA sequence database. However, in the case of KIR genes, the sequence database is incomplete.

The present invention describes a method whereby one or more exons of the KIR genes from multiple patients are sequenced at the same time and the KIR gene alleles present determined by a software program.

An exemplary software for the method of the present invention was developed by Conexio Genomics Pty. Ltd. (Fremantle, Western Australia). The software is able to unequivocally determine sequence identity in this gene family. A typical software useful in the invention would import the sequence data from the clonal sequencing device. In some embodiments, the flowgrams can also be imported in order to improve base call accuracy. In some embodiments, it is advantageous to consolidate the sequence reads in order to compress the data set. The software then identifies the sample tags (MID tags) and the primers. The use of tags allows multiple samples to be run together on a single plate. The software may be designed to permit base skipping or base insertion within the tag sites and to ensure that this will not lead to incorrect label assignment.

The software is capable of assessing the sequence homology with target locus and related genes that may be co-amplified, in order to assign the appropriate reference to each clone sequence. Since clones of DNA from all the target and co-amplified loci are mixed together within the emulsion PCR, it is necessary to identify the sequences by testing them against each of the loci that may be amplified in order to obtain a unique assignment. This process may be assisted by examining intron sequences to distinguish between loci.

The software is further capable of generating a consensus sequence for each target locus. This sequence contains a combination of bases from each of the two alleles in every locus. In the initial matching stage, the phase relationships between sequences are not considered.

In some embodiments of the invention, an initial typing may be made based on the sequence from each locus. This step is required when the genomic reference library is incomplete, and performing a full match on the genomic sequences will bias the results toward alleles that are not referenced in the non-coding regions. In some embodiments of the invention, a second level of typing may be undertaken, based on information in the introns. This enables one to refine the initial typing result in order to provide better resolution.

In some embodiments of the invention, the phase information from the clonal sequences may be used to provide complete and unambiguous allele matches within the sequenced region. The software will automatically handle cases where heterozygous sequence positions are spaced too far apart to permit complete phase resolution throughout the entire consensus.

Development of high-throughput allelic sequencing of the KIR complex as taught by the present invention is useful in studies of disease association. In some embodiments, the high-throughput allelic sequencing of the KIR complex allows prognosis of a disease or condition in an individual or predicting an individual's response to therapy based on the identity of the KIR gene alleles present in the individual's sample.

V. Sets and Kits

In one embodiment, the invention comprises a set of oligonucleotide primers for KIR sequencing. The set comprises primers that amplify a particular portion of the KIR genes. More specifically, the set includes one or more primer pairs suitable for amplification of exons or portions of exons in KIR genes. In some embodiments, the set includes primer pairs for amplifying each exon (or portion of each exon) in each KIR gene present in a patient. The primers in the set are preferably (but not necessarily) generic for all KIR genes, i.e. can amplify the same exon in all the KIR genes. The primers further contain additional sequences useful for emulsion PCR and high-throughput clonal sequencing. The additional sequences include an individual identification tag (MID tag) and an adapter, which includes and a library tag.

In some embodiments, the invention is a kit for amplifying and sequencing the KIR genes. The kit of the invention typically comprises multiple primer pairs suitable for amplifying the exons or portions of exons of KIR genes. The primer pairs comprise a forward primer, comprising an adapter region, an individual identification tag (MID tag) and a KIR-hybridizing region; and a reverse primer, comprising an adapter region, an individual identification tag (MID tag), and a KIR-hybridizing region. The kit of the invention often comprises primer pairs that amplify more that one exon in more than one KIR gene from multiple subjects. Often, the kit of the invention comprises sufficient number of primer pairs to determine the KIR genotype for all KIR genes in multiple individuals, e.g., 12 or more individuals. The primers may be gene-specific or generic to more than one KIR gene as exemplified in Table 2.

In some embodiments, a kit can additionally comprise one or more populations of beads that can be used in emulsion PCR. Each bead is conjugated to a primer capable of hybridizing to adapter regions of amplification primers. In some embodiments, a kit can comprise one or more containers with reaction components, for example, enzymes, buffers, nucleotides, control polynucleotides, and the like. The kit may also include additional reagents necessary for emulsion PCR and pyrosequencing as described for example, in U.S. Application Pub. No. 20100086914 and references cited therein.

VI. Reaction Mixtures

In one embodiment, the invention is a reaction mixture for KIR sequencing. The reaction mixture comprises a set of primers that amplify a particular portion of the KIR genes. The primers in the reaction mixture may contain additional sequences useful for emulsion PCR and high-throughput clonal sequencing. The additional sequences may include the MID tag, the adaptor and the library tag.

In some embodiments, the reaction mixture may additionally comprise one or more populations of beads, each bead conjugated to a primer capable of hybridizing to an adapter region of amplification primers. In some embodiments, the reaction mixture can comprise one enzymes, buffers and nucleotides. The reaction mixture may also include additional reagents necessary for emulsion PCR and pyrosequencing as described for example, in U.S. Application Pub. No. 20100086914 and references cited therein.

VII. Use of KIR Genotyping to Assess Disease Conditions

In some embodiments, the invention includes a method of detecting an individual's predisposition to a disease or condition by detecting the individual's KIR genotype.

In some embodiments, the method further includes determining the individual's HLA genotype, i.e. determining which HLA alleles are present in the individual. The HLA genotype may be determined by any method known in the art, including, without limitation, determining the HLA genotype using next generation sequencing, as described in Bentley et al., (2009) Tissue Antigens, 74:393-403.

In some embodiments, the method includes determining a woman's KIR genotype as described herein, and determining that the woman is predisposed to developing preeclampsia if it has been determined that a KIR2DL1 allele is present.

In other embodiments, the method includes determining an individual's KIR genotype as described herein, and determining that the individual is likely to clear an HCV infection if it has been determined that a KIR2DL3 allele is present. In some embodiments, the method further comprises determining the individual's HLA-C genotype and determining that the individual is likely to clear an HCV infection if it has been determined that a combination of KIR2DL3 allele and HLA-C1 allele are present.

In other embodiments, the method includes determining an individual's KIR genotype as described herein, and determining that the individual is less likely to progress from HIV infection to AIDS if it has been determined that a KIR3DS1 allele is present. In some embodiments, the method further comprises determining the individual's HLA genotype and determining that the individual is less likely to progress from HIV infection to AIDS if it has been determined that a combination of KIR3DS1 allele and HLA-Bw4 allele are present.

In yet other embodiments, the method includes determining an individual's KIR genotype as described herein, and determining that the individual is predisposed to developing an autoimmune disease if it has been determined that a KIR2DS1 allele is present.

In yet other embodiments, the method includes determining an individual's KIR genotype as described herein, and determining that the individual is predisposed to developing Crohn's disease if it has been determined that KIR2DL2/KIR2DL3 heterozygosity is present. In some embodiments, the method further comprises determining the individual's HLA genotype and determining that the individual is predisposed to developing Crohn's disease if it has been determined that a combination of KIR2DL2/KIR2DL3 heterozygosity and HLA-C2 allele are present.

In yet other embodiments, the method includes determining an individual's KIR genotype as described herein, and determining whether the individual is a suitable candidate for a donor in an unrelated hematopoietic cell transplantation if it has been determined that a group B KIR haplotype is present.

VII. Examples

Example 1

Obtaining the Sequences for Exon 5 in all KIR Genes in an Individual's Sample

As an example, 13 primer pairs suitable for amplification of all nine exons in the KIR genes are listed in Table 2. Each set of primers amplifies a single exon of the KIR genes, plus additional intronic sequence. Each primer also comprises a sample-specific identifier sequence, referred to as a Multiplex Identifier Tag (MID Tag), added at the 5'-end of each primer. Examples of the MID Tags are shown in Table 3. Each primer also includes a 4-bp library tag (not shown). These additional primer sequences are not shown in Table 2. Amplicon size shown in Table 2 includes the additional primer sequences: the 5-bp individual identification tag (MID Tag), and the 15-bp adapter sequence, including the 4-bp library tag.

TABLE 2

Exemplary KIR primers

| EXON | PRIMER | SPECIFICITY | AMPLICON SIZE (bp) | SEQUENCE 5' to 3' |
|---|---|---|---|---|
| 1 | KAP061F | generic | 136 | CATCCTGTGYGCTGCTG |
|  | KAP063R | generic |  | ATTCCYTTCCAGGACTCACC |
| 2 | KAP064F | generic | 206 | GTCCATCATGATCTTTCTTS |
|  | KAP066R | generic |  | GGTTTGGRGAAGGACTCACC |

TABLE 2-continued

Exemplary KIR primers

| EXON | PRIMER | SPECIFICITY | AMPLICON SIZE (bp) | SEQUENCE 5' to 3' |
|---|---|---|---|---|
| 3 | KAP067F<br>KAP069R | generic<br>(except 2DL4)<br>2DL1, 2DS1,<br>2DS2, 2DS3,<br>2DS5, 3DP1 | 381 | CCACATCCTCCTYTCTAAGG<br>GGACAAGGAGAATCCMAGAC |
| 3 | KAP067F<br>KAP070R | 2DL1, 2DS1,<br>2DS3, 2DS4,<br>3DL1, 3DL3,<br>3DS1, 3DP1<br>generic | 381 | CCACATCCTCCTYTCTAAGG<br>GGACAAGGAGAAGCCCAGAC |
| 3 | KAP068F<br>KAP070R | 2DL4<br>generic | 381 | CAACATACTCCTCTCTGAGG<br>GGACAAGGAGAAGCCCAGAC |
| 4 | KAP071F<br>KAP073R | generic<br>(except 3DL3)<br>generic | 443 | CATGGATGGGATGATAAAGAGAGA<br>CCAAGTCSTGGATCATTCACTC |
| 5 | KAP085F<br>KAP086R | generic<br>(except 2DL5)<br>generic | 377 | CCTCTTCTCCTTCCAGGTC<br>GCAGGAAGCTCCTYAGCTA |
| 5 | KAP075F<br>KAP086R | 2DL5<br>generic | 377 | CTGCCTCTTCTTCCAGGTC<br>GCAGGAAGCTCCTYAGCTA |
| 6 | KAP092F<br>KAP080R | generic<br>(except 2DL5)<br>generic | 147 | CTCCTGTCTCATGTTCTAGGAAAC<br>GTTTCHACCTCCCCAGG |
| 6 | KAP093F<br>KAP080R | 2DL5<br>generic | 147 | CTCCTGTCCTGTGTTCTAGGAAAC<br>GTTTCHACCTCCCCAGG |
| 7 | KAP087F<br>KAP082R | generic<br>generic | 243 | AACTGCTATGATTAGCTTCTTA<br>GCTMCCATCCTGCTTCC |
| 8 | KAP083F<br>KAP084R | generic<br>generic | 143 | CTTATGAAATGAGGRCCCAGAAG<br>GGCCGAGGAGNACCTACC |
| 9 | KAP089F<br>KAP090R | generic<br>generic | 327-347 | CCTCACTCAGCATTTCCCTC<br>CTTCAGATTCCAGCTGCTGG |

Y: C or T,
R: A or G,
H: A, C or T,
M: A or C,
N: A, C, G or T

TABLE 3

Exemplary MID Tags.

| Primer | MID (multiplex identifier) |
|---|---|
| 1 forward | TCTCT |
| 1 reverse | TCTCA |
| 2 forward | TGCAT |
| 2 reverse | TCTGA |
| 3 forward | ATCAT |
| 3 reverse | TCAGA |
| 4 forward | ATGAT |
| 4 reverse | TGAGA |
| 5 forward | ATGCT |
| 5 reverse | ATGCA |
| 6 forward | AGCAT |
| 6 reverse | AGAGA |
| 7 forward | CTCAT |
| 7 reverse | CTGCA |
| 8 forward | CTGAT |
| 8 reverse | CAGCA |

In the example, the KIR sequence from 8 samples obtained from the National Marrow Donor Program were amplified using the primers shown in Table 2. The amplified nucleic acids were purified using Agencourt DNA purification system (Beckman Coulter, Brea, Calif.). The purified nucleic acids were quantified and diluted to an appropriate concentration. The nucleic acids were then pooled together to form a pool of all amplicons from all samples. An aliquot of this mixture was prepared for sequencing using the pyrosequencing protocol of the 454 GS-FLX platform (454 Life Sciences, Branford, Conn.). The sequencing data was analyzed by Conexio ATF software (Conexio Genomics, Fremantle, Aus.).

FIGS. 3 and 4 show the sequence of exon 5 for all KIR genes. The italicized nucleotides are unique for a particular KIR gene in exon 5; thus any sequence attached to that particular sequence motif is immediately distinguished from other KIR genes. The bold nucleotides are shared among several of the KIR genes, but not all. The nucleotides boxed in grey are polymorphic in the KIR gene.

The results illustrate that longer sequencing runs (300 bp) are necessary to differentiate these genes. As can be seen from FIG. 4, with sequencing runs that could only sequence 50 to 60 base pairs, as was done in the prior art, one would not have been able to distinguish the KIR genes 2DL2, 2DL3, 2DS3, 2DS5, or 2DP1.

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A method of determining KIR genotypes by determining sequences of multiple exons in multiple KIR genes for one or more individuals in parallel, the method comprising:
   (a) for each individual, performing an amplification reaction for each KIR exon with a single forward primer and a single reverse primer, each primer comprising an adapter sequence, an individual identification sequence, and a KIR-hybridizing sequence hybridizing to and supporting amplification of the sequence from the same exon in more than one KIR gene, to amplify the exon sequences of more than one KIR genes that comprise polymorphic sites to obtain amplicons from more than one KIR gene;
   (b) pooling KIR amplicons from more than one individual obtained in step (a);
   (c) performing emulsion PCR;
   (d) determining the sequence of each KIR amplicon for each individual using pyrosequencing in parallel; and
   (e) assigning the KIR alleles to each individual by comparing the sequence of the KIR amplicons determined in step (d) to known KIR sequences to determine which KIR alleles are present in the individual thereby determining the KIR genotype.

2. The method of claim 1, further comprising determining the KIR haplotypes present in each individual.

3. The method of claim 1, wherein step (a) further comprises determining concentration of said KIR amplicons.

4. The method of claim 1, wherein at least one primer has the KIR- hybridizing sequence selected from Table 2.

5. The method of claim 1, wherein at least one primer has an individual identification sequence selected from Table 3.

6. The method of claim 1, further comprising step (f) of determining that the individual is predisposed to preeclampsia when allele KIR2DL1 has been found in step (e).

7. The method of claim 1, further comprising step (f) of determining that the individual is predisposed to autoimmune disease when allele KIR2DS1 has been found in step (e).

8. The method of claim 1, further comprising step (f) of determining that the individual is a suitable unrelated hematopoietic stem cell donor when group B KIR alleles have been found in step (e).

9. The method of claim 1, further comprising step (f) of determining the individual's HLA genotype.

10. The method of claim 9, further comprising step (g) of determining that the individual is predisposed to clearing an HCV infection when allele KIRDL1 has been found in step (e) and allele HLA-C1 has been found in step (f).

11. The method of claim 9, further comprising step (g) of determining that the individual is predisposed to slow progression of HIV infection to AIDS when allele KIR3DS1 has been found in step (e) and allele HLA-Bw4 has been found in step (f).

12. The method of claim 9, further comprising step (g) of determining that the individual is predisposed to Crohn's disease when alleles KIR2DL2 and KIR2DL3 have been found in step (e) and allele HLA-C2 has been found in step (f).

* * * * *

SEQUENCE LISTING

```
<160> NUMBER OF SEQ ID NOS: 58

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
catcctgtgy gctgctg                                                     17

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
attccyttcc aggactcacc                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtccatcatg atctttctts                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtttggrga aggactcacc                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 5
ccacatcctc ctytctaagg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggacaaggag aatccmagac                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccacatcctc ctytctaagg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggacaaggag aagcccagac                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caacatactc ctctctgagg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggacaaggag aagcccagac                                              20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catggatggg atgataaaga gaga                                          24

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccaagtcstg gatcattcac tc                                            22

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cctcttctcc ttccaggtc                                                19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcaggaagct cctyagcta                                                19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctgcctcttc ttccaggtc                                                19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcaggaagct cctyagcta                                                19

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 17
ctcctgtctc atgttctagg aaac                                              24

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtttchacct ccccagg                                                      17

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctcctgtcct gtgttctagg aaac                                              24

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtttchacct ccccagg                                                      17

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aactgctatg attagcttct ta                                                22

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctmccatcc tgcttcc                                                      17

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 23
cttatgaaat gaggrcccag aag                                              23

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (11)..(11)
<223> OTHER INFORMATION: a, c, t, g, unknown or other

<400> SEQUENCE: 24
ggccgaggag nacctacc                                                    18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cctcactcag catttccctc                                                  20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cttcagattc cagctgctgg                                                  20

<210> SEQ ID NO 27
<211> LENGTH: 149
<212> TYPE: DNA
<213> ORGANISM: Homo sapiens

<400> SEQUENCE: 27
gtctatatga gaaaccttct ctctcagccc agccgggccc cacggttctg gcaggagaga      60
atgtgacctt gtcctgcagc tcccggagct cctatgacat gtaccatcta tccagggaag    120
gggaggccca tgaacgtagg ctccctgca                                      149

<210> SEQ ID NO 28
<211> LENGTH: 149
<212> TYPE: DNA
<213> ORGANISM: Homo sapiens

<400> SEQUENCE: 28
gtctatatga gaaaccttct ctctcagccc agccgggccc cacggttctg gcaggagaga      60
gcgtgacctt gtcctgcagc tcccggagct cctatgacat gtaccatcta tccagggagg    120
gggaggccca tgaatgtagg ttctctgca                                      149

```
<210> SEQ ID NO 29
<211> LENGTH: 149
<212> TYPE: DNA
<213> ORGANISM: Homo sapiens

<400> SEQUENCE: 29
gtctatatga gaaaccttct ctctcagccc agccgggccc cacggttctg gcaggagaga        60
gcgtgacctt gtcctgcagc tcccggagct cctatgacat gtaccatcta tccagggagg       120
gggaggccca tgaacgtagg ttctctgca                                         149

<210> SEQ ID NO 30
<211> LENGTH: 149
<212> TYPE: DNA
<213> ORGANISM: Homo sapiens

<400> SEQUENCE: 30
gtctatatga gaaaccttcg cttacagccc ggccgggccc cacggttcgc acaggagaga        60
acgtgacctt gtcctgcagc tcccagagct cctttgacat ctaccatcta tccagggaag       120
gggaagccca tgaacttagg ctccctgca                                         149

<210> SEQ ID NO 31
<211> LENGTH: 149
<212> TYPE: DNA
<213> ORGANISM: Homo sapiens

<400> SEQUENCE: 31
gtctatttgg gaaaccttca ctctcagccc agccgggccc cacggttcgc acaggagaga        60
acgtgacctt gtcctgcagc tccaggagct catttgacat gtaccatcta tccagggagg       120
ggagggccca tgaacctagg ctccctgca                                         149

<210> SEQ ID NO 32
<211> LENGTH: 149
<212> TYPE: DNA
<213> ORGANISM: Homo sapiens

<400> SEQUENCE: 32
gtctatatga gaaaccttct ctctcagccc agccgggccc cacggttctg gcaggagaga        60
atgtgacctt gtcctgcagc tcccggagct cctatgacat gtaccatcta tccagggaag       120
gggaggccca tgaacgtagg ctccctgca                                         149

<210> SEQ ID NO 33
<211> LENGTH: 149
<212> TYPE: DNA
<213> ORGANISM: Homo sapiens

<400> SEQUENCE: 33
gtctatatga gaaaccttct ctctcagccc agccgggccc cacggttttg gcaggagaga        60
gcgtgacctt gtcctgcagc tcccggagct cctatgacat gtaccatcta tccagggagg       120
gggaggccca tgaacgtagg ttctctgca                                         149

<210> SEQ ID NO 34
<211> LENGTH: 149
<212> TYPE: DNA
<213> ORGANISM: Homo sapiens
```

```
<400> SEQUENCE: 34
gtctatatga gaaaccttct ctctcagccc agccgggccc cacggttctg gcaggagaga    60
gcgtgacctt gtcctgcagc tcctggagct cctatgacat gtaccatcta tccacggagg   120
gggaggccca tgaacgtagg ttctctgca                                      149

<210> SEQ ID NO 35
<211> LENGTH: 149
<212> TYPE: DNA
<213> ORGANISM: Homo sapiens

<400> SEQUENCE: 35
gtctatatga gaaaccttct ctctcagccc agccgggccc cacggttcag gcaggagaga    60
atgtgacctt gtcctgcagc tcccggagct cctatgacat gtaccatcta tccagggaag   120
gggaggccca tgaacgtagg ctccctgca                                      149

<210> SEQ ID NO 36
<211> LENGTH: 149
<212> TYPE: DNA
<213> ORGANISM: Homo sapiens

<400> SEQUENCE: 36
gtctatatga gaaaccttct ctcccagccc agccgggccc cacggttctg gcaggagaga    60
gcgtgacctt gtcctgcagc tcccggagct cctatgacat gtaccatcta tccagggaag   120
gggaggccca tgaacgtagg ctccctgca                                      149

<210> SEQ ID NO 37
<211> LENGTH: 149
<212> TYPE: DNA
<213> ORGANISM: Homo sapiens

<400> SEQUENCE: 37
gtccatatga gaaaccttct ctctcagccc agccgggccc caaggttcag gcaggagaga    60
gcgtgacctt gtcctgtagc tcccggagct cctatgacat gtaccatcta tccagggagg   120
ggggagccca tgaacgtagg ctccctgca                                      149

<210> SEQ ID NO 38
<211> LENGTH: 149
<212> TYPE: DNA
<213> ORGANISM: Homo sapiens

<400> SEQUENCE: 38
gtctatatga gaaaccttct ctctcagccc agccgggccc cacggttcag gcaggagaga    60
acgtgacctt gtcctgtagc tcctggagct cctatgacat ctaccatctg tccagggaag   120
gggaggccca tgaacgtagg ctccgtgca                                      149

<210> SEQ ID NO 39
<211> LENGTH: 149
<212> TYPE: DNA
<213> ORGANISM: Homo sapiens

<400> SEQUENCE: 39
gtctatatgg gaaaccttct ctctcagccc agccgggccc cacggttcag gcaggagaga    60
atgtgacctt gtcctgcagc tcccggagct tgtttgacat ttaccatcta tccagggagg   120
cagaggccgg tgaacttagg ctcactgcg                                      149
```

```
<210> SEQ ID NO 40
<211> LENGTH: 149
<212> TYPE: DNA
<213> ORGANISM: Homo sapiens

<400> SEQUENCE: 40
gtctatatga gaaaccttct ctctcagccc agccgggccc caaggttcag gcaggagaga      60
gcgtgacctt gtcctgtagc tcccggagct cctatgacat gtaccatcta tccagggagg    120
ggggagccca tgaacgtagg ctccctgca                                       149

<210> SEQ ID NO 41
<211> LENGTH: 149
<212> TYPE: DNA
<213> ORGANISM: Homo sapiens

<400> SEQUENCE: 41
gtctatatga gaaaccttct ctctcagccc agccgggccc cacggttctg gcaggagaga      60
gcgtgacctt gtcctgcagc tcccggagct cctatgacat gtaccatcta tccacggagg    120
gggaggccca tgaacgtagg ttctctgca                                       149

<210> SEQ ID NO 42
<211> LENGTH: 149
<212> TYPE: DNA
<213> ORGANISM: Homo sapiens

<400> SEQUENCE: 42
gtctatgtgg gaaaccttct ctctcagccc agccgcgccc catggttaag gcaggagaga      60
gcgtgacctt gtcctgcagc tcccggagct cctatgacat ctaccatcta tcaagggacg    120
gggaggctca tgaacttagg ttccctgca                                       149

<210> SEQ ID NO 43
<211> LENGTH: 145
<212> TYPE: DNA
<213> ORGANISM: Homo sapiens

<400> SEQUENCE: 43
gggcccaagg tcaacggaac attccaggct gactttcctc tgggccctgc cacccacgga      60
gggacctaca gatgcttcgg ctctttccat gactctccat acgagtggtc aaagtcaagt    120
gacccactgc ttgtttctgt cacag                                           145

<210> SEQ ID NO 44
<211> LENGTH: 145
<212> TYPE: DNA
<213> ORGANISM: Homo sapiens

<400> SEQUENCE: 44
gggcccaagg tcaacggaac attccaggcc gactttcctc tgggccctgc cacccacgga      60
ggaacctaca gatgcttcgg ctctttccgt gactctccat acgagtggtc aaactcgagt    120
gacccactgc ttgtttctgt catag                                           145

<210> SEQ ID NO 45
<211> LENGTH: 145
<212> TYPE: DNA
<213> ORGANISM: Homo sapiens
```

```
<400> SEQUENCE: 45
gggcccaagg tcaacggaac attccaggcc gactttcctc tgggccctgc cacccacgga      60
ggaacctaca gatgcttcgg ctctttccgt gactctccat acgagtggtc aaactcgagt     120
gacccactgc ttgtttctgt cacag                                           145

<210> SEQ ID NO 46
<211> LENGTH: 145
<212> TYPE: DNA
<213> ORGANISM: Homo sapiens

<400> SEQUENCE: 46
gtgcccagca tcaatggaac attccaggcc gacttccctc tgggtcctgc cacccacgga      60
gagacctaca gatgcttcgg ctctttccat ggatctccct acgaatggtc agacgcgagt     120
gacccactgc ctgtttctgt cacag                                           145

<210> SEQ ID NO 47
<211> LENGTH: 145
<212> TYPE: DNA
<213> ORGANISM: Homo sapiens

<400> SEQUENCE: 47
gtgcccagcg tcaatggaac attccaggct gactttcctc tgggccctgc cacccacgga      60
gggacctaca catgcttcgg ctctctccat gactcaccct atgagtggtc agacccgagt     120
gacccactgc ttgtttctgt cacag                                           145

<210> SEQ ID NO 48
<211> LENGTH: 145
<212> TYPE: DNA
<213> ORGANISM: Homo sapiens

<400> SEQUENCE: 48
gggaccaagg tcaacggaac attccaggcc aactttcctc tgggccctgc cacccatgga      60
gggacctaca gatgcttcgg ctctttccgt gactctccat acgagtggtc aaagtcaagt     120
gacccactgc ttgtttctgt cacag                                           145

<210> SEQ ID NO 49
<211> LENGTH: 145
<212> TYPE: DNA
<213> ORGANISM: Homo sapiens

<400> SEQUENCE: 49
gggcccaagg tcaacggaac attccaggcc gactttcctc tgggccctgc cacccacgga      60
ggaacctaca gatgcttcgg ctctttccgt gactctccct atgagtggtc aaactcgagt     120
gacccactgc ttgtttctgt cacag                                           145

<210> SEQ ID NO 50
<211> LENGTH: 145
<212> TYPE: DNA
<213> ORGANISM: Homo sapiens

<400> SEQUENCE: 50
gggcccaagg tcaacggaac attccaggcc gactttcctc tgggccctgc cacccaagga      60
ggaacctaca gatgcttcgg ctctttccat gactctccct acgagtggtc aaagtcaagt     120
gacccactgc ttgtttctgt cacag                                           145
```

```
<210> SEQ ID NO 51
<211> LENGTH: 145
<212> TYPE: DNA
<213> ORGANISM: Homo sapiens

<400> SEQUENCE: 51
gtgcgcagca tcaacggaac attccaggcc gactttcctc tgggccctgc cacccacgga      60
gggacctaca gatgcttcgg ctctttccgt gacgctccct acgagtggtc aaactcgagt     120
gatccactgc ttgtttccgt cacag                                           145

<210> SEQ ID NO 52
<211> LENGTH: 145
<212> TYPE: DNA
<213> ORGANISM: Homo sapiens

<400> SEQUENCE: 52
gggcccaagg tcaacagaac attccaggcc gactctcctc tggaccctgc cacccacgga      60
ggggcctaca gatgcttcgg ctctttccgt gactctccat acgagtggtc aaagtcaagt     120
gacccactgc ttgtttctgt cacag                                           145

<210> SEQ ID NO 53
<211> LENGTH: 145
<212> TYPE: DNA
<213> ORGANISM: Homo sapiens

<400> SEQUENCE: 53
gtgcgcaagg tcaacagaac attccaggca gatttccctc tgggccctgc cacccacgga      60
gggacctaca gatgcttcgg ctctttccgt cactctccct acgagtggtc agacccgagt     120
gacccactgc ttgtttctgt cacag                                           145

<210> SEQ ID NO 54
<211> LENGTH: 145
<212> TYPE: DNA
<213> ORGANISM: Homo sapiens

<400> SEQUENCE: 54
gtgcccaagg tcaacagaac attccaggca gactttcctc tgggccctgc cacccacgga      60
gggacctaca gatgcttcgg ctctttccgt gccctgccct gcgtgtggtc aaactcaagt     120
gacccactgc ttgtttctgt cacag                                           145

<210> SEQ ID NO 55
<211> LENGTH: 145
<212> TYPE: DNA
<213> ORGANISM: Homo sapiens

<400> SEQUENCE: 55
gtgctgaggg tcaatggaac attccaggcc aacttccctc tgggccctgt gacccacgga      60
gggaactaca gatgcttcgg ctctttccgt gccctgcccc acgcgtggtc agacccgagt     120
gacccactgc ccgtttctgt cacag                                           145

<210> SEQ ID NO 56
<211> LENGTH: 145
<212> TYPE: DNA
<213> ORGANISM: Homo sapiens
```

```
<400> SEQUENCE: 56
gtgcgcaagg tcaacagaac attccaggca gatttccctc tgggccctgc cacccacgga      60
gggacctaca gatgcttcgg ctctttccgt cactctccct acgagtggtc agacccgagt     120
gacccactgc ttgtttctgt cacag                                           145

<210> SEQ ID NO 57
<211> LENGTH: 145
<212> TYPE: DNA
<213> ORGANISM: Homo sapiens

<400> SEQUENCE: 57
gggcccaagg tcaacggaac attccaggct gactttcctc tgggccctgc cacccacgga      60
ggaacctaca gatgcttcgg ctctttccgt gactctccct acgagtggtc aaactcgagt     120
gacccactgc ttgtttctgt cacag                                           145

<210> SEQ ID NO 58
<211> LENGTH: 145
<212> TYPE: DNA
<213> ORGANISM: Homo sapiens

<400> SEQUENCE: 58
gtgcccaagg tcaatggaac cttccaggcc aactttcctc tgggccctgc cacccacgga      60
gggacctaca gatgcttcgg ctctttccgt gactctccct acgagtggtc agaccttagt     120
gacccactgc ttgtttctgt cacag                                           145
```